(12) United States Patent
Lavoie et al.

(10) Patent No.: US 6,571,812 B1
(45) Date of Patent: Jun. 3, 2003

(54) UNIVERSAL SHELVING SYSTEM (75) Inventors: Patrice Lavoie, Val-Belair (CA); Denis Belanger, Beauport (CA)

(73) Assignee: Steris Inc., Temecula, CA (US)

( * ) Notice: Subject to any disclaimer, the term of this patent is extended or adjusted under 35 U.S.C. 154(b) by 94 days.

(21) Appl. No.: 09/777,447

(22) Filed: Feb. 6, 2001

Related U.S. Application Data (60) Provisional application No. 60/181,440, filed on Feb. 10, 2000.

(51) Int. Cl.[7] .............................. A47L 15/16; A47L 15/50
(52) U.S. Cl. ........................ 134/191; 134/195; 134/199; 134/201; 312/228.1
(58) Field of Search ............................... 134/44, 54, 55, 134/171, 180, 181, 191, 195, 198, 199, 200, 201; 211/41.8, 41.9; 312/228.1, 311

(56) References Cited

U.S. PATENT DOCUMENTS

| | | | |
|---|---|---|---|
| 3,466,109 A | * | 9/1969 | Kauffman et al. ....... 312/228.1 |
| 3,486,804 A | * | 12/1969 | Kauffman et al. ....... 312/228.1 |
| 4,552,728 A | | 11/1985 | Taylor |
| 4,708,153 A | | 11/1987 | Hambleton et al. |
| 4,865,821 A | | 9/1989 | Langdon |
| 4,909,401 A | | 3/1990 | McConnell |
| 5,424,048 A | | 6/1995 | Riley |
| 5,507,398 A | | 4/1996 | Miller |
| 5,749,385 A | | 5/1998 | Rochette et al. |
| 5,769,520 A | | 6/1998 | Jun et al. |
| 5,904,162 A | | 5/1999 | Ferguson et al. |
| 5,906,801 A | | 5/1999 | Goughnour |

* cited by examiner

Primary Examiner—Philip R. Coe
(74) Attorney, Agent, or Firm—Fay, Sharpe, Fagan, Minnich & McKee, LLP (57) ABSTRACT

A decontamination device (10) includes a washing chamber (12) defined by a series of sidewalls. Upper and lower shelves (30, 32) are horizontally disposed within the washing chamber. The lower shelf is a rigid non-removable structure divided into three washing sections (42, 44, 46). The upper shelf is disposed vertically above the lower shelf and is slidably mounted within the washing chamber. The upper shelf comprises first, second, and third washing sections (82a, 82b, 82c) and a channel (78) operatively connected to the three shelf sections. The channel provides cleaning solutions to the shelf sections. Each of the washing sections and the shelf sections receive a spindle header (50) having a series of spindles (58) over which glassware is placed. A sealing connector, disposed on each washing section and shelf section, registers with and seals around a manifold of the spindle header and provides cleaning solutions from the channel to the spindle header. The second and third shelf sections of the upper shelf are selectively and individually removable from the washing chamber which provides additional height for larger glassware articles on the lower shelf.

20 Claims, 11 Drawing Sheets

UNIVERSAL SHELVING SYSTEM

This application claims the benefit of provisional application No. 60/181,440 filed on Feb. 10, 2000.

BACKGROUND OF THE INVENTION

The present invention relates generally to the cleaning and decontamination art. It finds particular application in the washing, sterilizing and disinfecting apparatus typically employed to clean, sterilize and disinfect laboratory glassware, such as volumetric flasks, beakers, test tubes, and the like, and will be described with particular reference thereto. It will be appreciated, however, that the invention may be applicable to a wide variety of apparatus used in sanitizing.

Flasks, beakers, test tubes and other glassware which are commonly used in laboratories are thoroughly cleaned after use in order to remove deposits which could contaminate materials subsequently contained in the glassware. Glassware is often cleaned manually with a brush. However, this manual procedure is generally undesirable because it requires considerable time and effort which could be spent on more productive tasks.

To minimize manual cleaning time, several laboratory glassware washing machines have been introduced. Known laboratory glassware washing machines operate analogous to household dishwashers wherein glassware is inverted and the mouth and neck are received by a spindle extending vertically from a rack. The rack is selectively moveable in and out of a washing chamber of the machine. Optionally, a second slidable rack is provided above the first rack for accommodating additional glassware. At least one spray arm is typically located beneath the rack which applies upwardly directed wash and rinse sprays for washing and rinsing the glassware. Heated air for drying the glassware is circulated within the washer chamber during the drying cycle.

Although this type of machine effectively cleans and dries a variety of different types of glassware articles, it has some drawbacks. Beakers, flasks, test tubes and other types of glassware come in many different sizes and shapes. For example, test tubes are generally smaller in width and height than beakers. In addition, graduated cylinders are manufactured having a wide range of heights and diameters. Flasks and beakers are typically enlarged at bottom portions and require more room when being washed. Known glassware washing machines are typically configured to accommodate only a limited range of sizes and configurations of beakers, flasks and test tubes.

As already noted, known glassware washing machines typically have racks which are slidable in and out of the washing chamber. Spindles extend vertically upward from the racks and receive the mouth and neck of the glassware. The height of the spindle directly relates to the height of the particular glassware to be washed. For example, a tall piece of glassware is typically received by a relatively tall spindle for adequate support during glassware washing operations. In contrast, a shorter piece of glassware is placed on a shorter spindle. Moreover, glassware with larger diameters, such as bulb shaped flasks, need additional spacing between adjacent spindles. Known glassware washing machines generally include a series of evenly spaced spindles having a uniform height. As such, these devices do not efficiently accommodate the needs of glassware articles having differing sizes and shapes.

To overcome the foregoing shortcomings, one known device is manufactured having a removable and replaceable rack system. Such a system allows an operator to choose from multiple complete racks each having spindles designed to receive a particular size of glassware. Therefore, the washer is adapted to sanitize multiple sizes of glassware. Although this device is capable of washing several sizes and shapes of glassware, it does so in separate washing cycles and therefore is not capable of washing differing articles at the same time. This has obvious efficiency problems due to the increased time which elapses during the several washing intervals.

In addition, washers of the foregoing nature are relatively large and constructed of heavy material. Because the racks are bulky and awkward, they are difficult to handle during changing periods and often require the work of at least two people. Additional workers add to the cost operation and slow the changeover process.

Additional problems are created when glassware washing machines are constructed with two or more levels of racks. If the height of a glassware article is greater than the spacing between the top and bottom rack or the spacing between the top rack and the top of the washing chamber, the washer will be unable to clean the article. The work may be done manually or the top rack can be removed to provide additional height for larger articles. However, removing the top rack cuts the capacity in half. When there are only one or a few tall articles, significant washing potential is lost. Such a device may again need additional workers to remove the heavy and awkward top shelf.

The present invention provides a new and improved construction which overcomes the above-referenced problems and others.

SUMMARY OF THE INVENTION

In accordance with one aspect of the present invention, a decontamination unit comprises a washing chamber defined by a series of walls. A first shelf is mounted within the washing chamber. The first shelf has at least one washing section for receiving and supporting articles to be cleaned during operation of the decontamination unit. A second shelf is slidably mounted within the washing chamber vertically above the first shelf. The second shelf has at least two shelf sections that are operatively associated. At least one of the shelf sections is selectively detachable from the second shelf and removable from the washing chamber so that additional space may be provided for larger articles that need to be decontaminated.

In accordance with another aspect of the present invention, a shelving assembly for a decontamination unit comprises a shelf having at least two shelf sections that are operatively associated. Each of the two shelf sections has a surface for carrying a set of articles to be cleaned. At least one of the shelf sections is detachable and removable from the shelf. A channel is operatively connected to each of the shelf sections for providing decontamination solutions to the articles to be cleaned. At least one support member is mounted to an outer edge of the shelf for allowing the shelving assembly to be slidably mounted within a decontamination device.

A first advantage of the present invention is that it provides greater flexibility and efficiency in decontaminating diverse sizes of glassware articles simultaneously.

Another advantage of the present invention is that the device can be changed over between different configurations quickly with minimal labor.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED INVENTION

Figure 1:
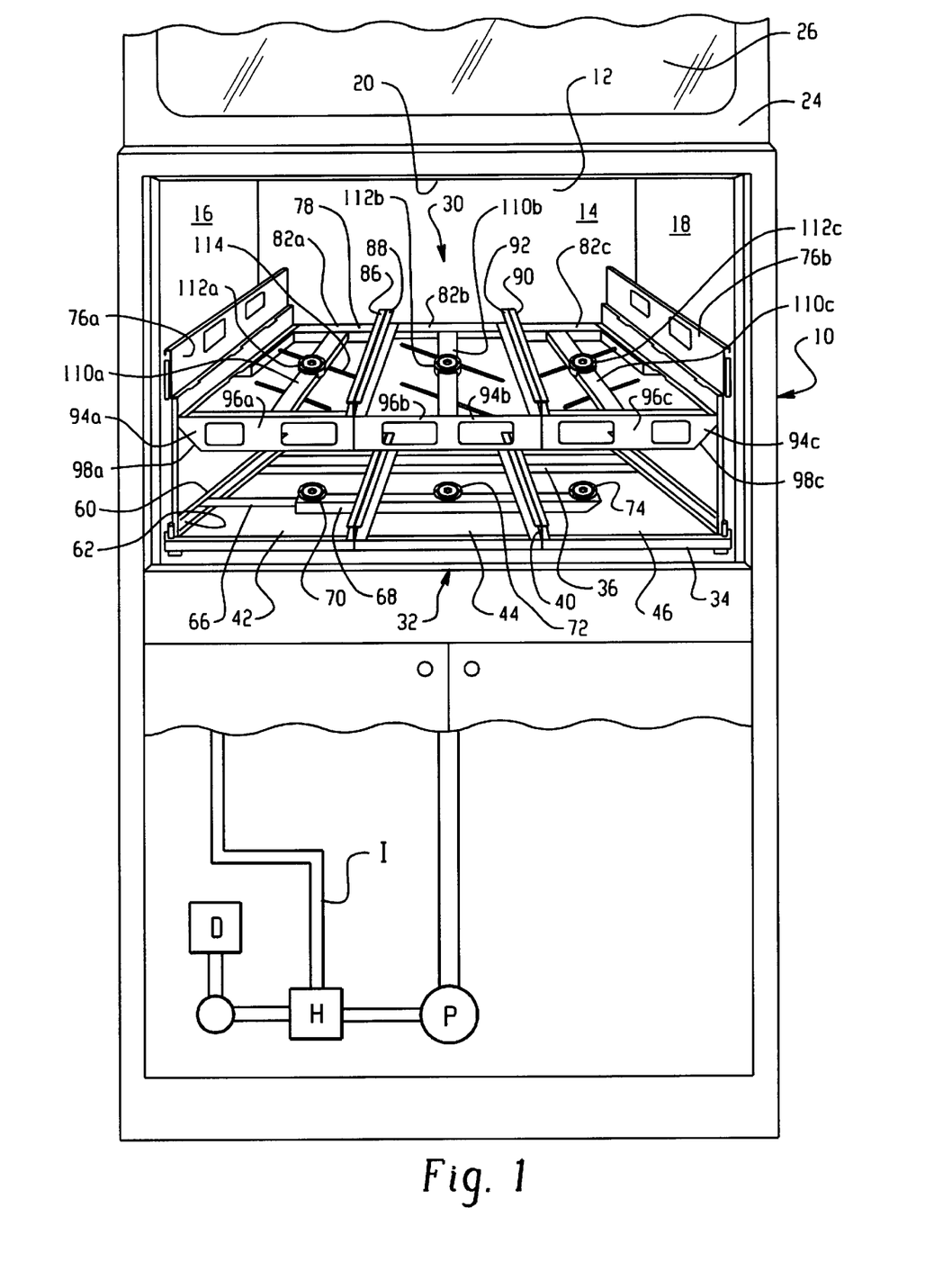
FIG. 1 is a front perspective view of a washing device with its front closure raised to expose the interior and with its spindle sections removed in accordance with the present invention.
Figure 2:
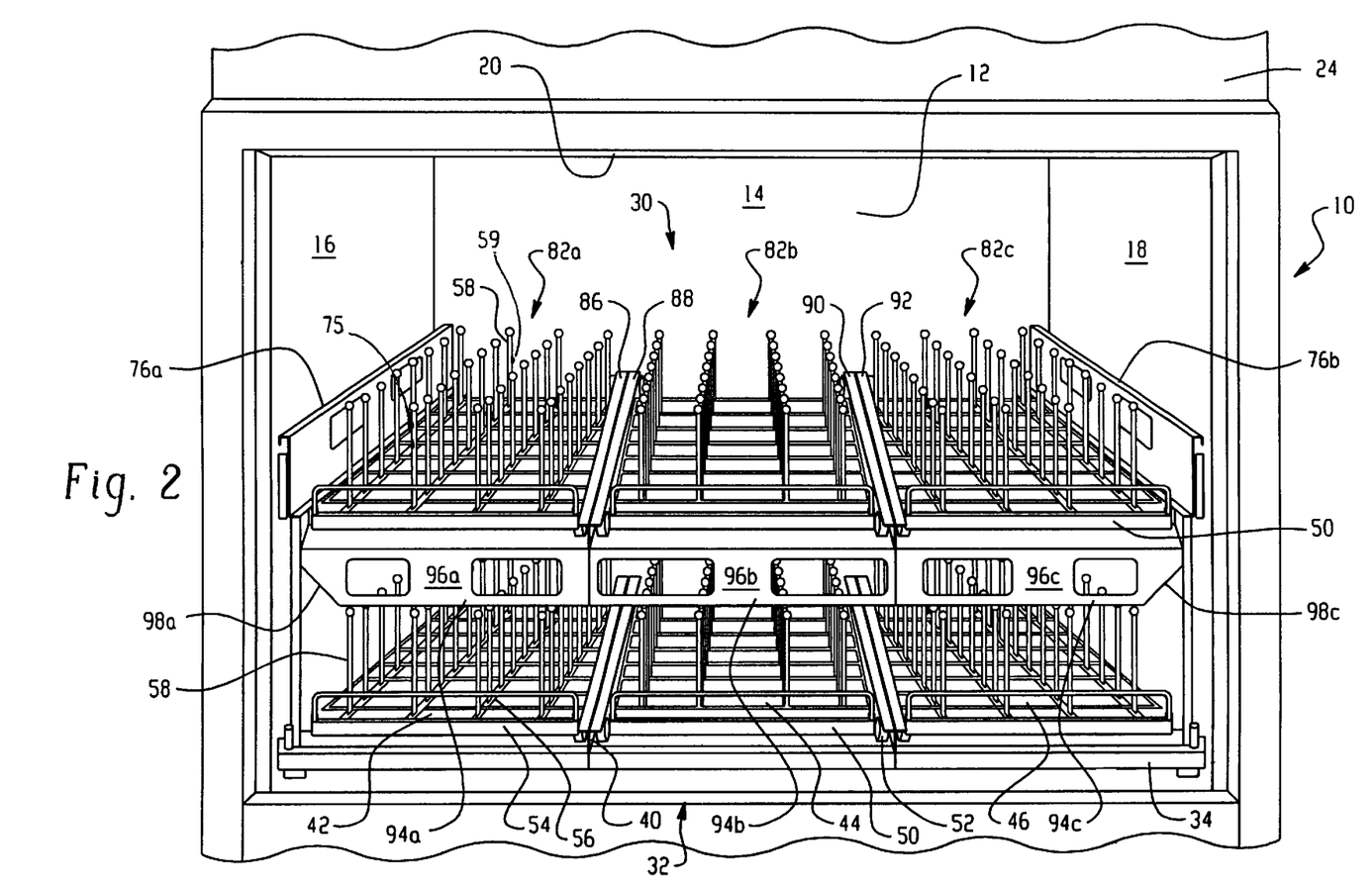
FIG. 2 is a front perspective view of a washing device of FIG. 1 having a series of spindle headers disposed therein.

With reference to FIGS. 1 and 2, a washing device 10 includes a washing chamber 12 defined by a back wall 14, opposing sidewalls 16, 18 and opposing top and bottom walls 20, 22. A vertically sliding door 24, having a window 26 formed integrally therewith, slides vertically downward to close the washing chamber during operation. Upper shelf 30 and a lower shelf 32 are horizontally disposed within the washing chamber and are preferably made of stainless steel. However, it will be appreciated that the washing device can be manufactured having any desired number of shelves including only one, three, etc.

A pump P, located in a cabinet beneath the washing device 10, pushes water through a heater H and into an injector I that communicates with the upper and lower shelves 30, 32. A detergent dispenser D communicates with the injector and provides detergent to be mixed with the heated water. The pump P is a two speed pump. When the upper shelf is not being used or is removed, the amount of pressure needed to provide cleaning solution to the washing chamber is decreased. As such, the pump operates at a first lower speed. When the upper shelf is being used, the system needs more pressure. Thus, the pump operates at a second higher speed.

The lower shelf 32 is preferably a rigid, non-removable structure comprising a pair of transverse horizontal beams 34, 36 disposed in parallel relation which span the two opposing sidewalls 16, 18. A series of C-channels or tracks 40 each extend perpendicularly from a top surface of one beam to a top surface of the other beam, effectively dividing the lower shelf into equally sized first, second, and third washing sections 42, 44, 46. However, a lower shelf with any desired number of washing sections, such as two or four is within the scope of the present invention. The series of tracks are arranged in such a manner that each washing section has a pair tracks 40 spaced from one another in parallel relation so that their open channels are facing each other.

Each washing section carries a spindle header or rack 50 having an effective width equal to the distance between the pair of tracks of each washing section. The racks are supported by wheels 52 which enables them to be easily rolled in and out of the C-channels of the washing sections. It will be appreciated, however, that the rack may be supported by any other means such as low coefficient of friction slide blocks. The racks 50 each include an essentially rectangular frame 54 and a grid of supports 56 running the width and length of the rectangular frame. Extending vertically upward from the grid of supports 56 are a plurality of spindles 58 over which glassware, such as beakers, flasks, and test tubes can be placed for washing. Nozzles 59 on each spindle direct fluid to the interior of each piece of glassware. The spindle size and spacing varies with each rack in order to accommodate different sizes of glassware. In the illustrated embodiment, up to three different types of racks can be inserted into the three washing sections of the lower shelf at any given time.

Horizontally extending upper and lower flanges 60, 62 of the C-channels prevent substantial vertical movement of the racks during washing operations. The lower flange 62 of the C-channel is wider than the upper flange 60. To prevent backward and forward movement of the racks during operation, the rack wheels fall into apertures (not shown) located at predetermined positions along the lower flange of the C-channels. Alternatively, recesses, protrusions, or bumps may be provided to hinder forward and backward movement of the racks.

In order to provide water, soap, etc. to the lower shelf 32, a member 66 extends perpendicularly from sidewall 16 and travels beneath the lower shelf until it terminates at the approximate center of the third washing section 46. A substantially rectangular channel 68 distributes washing liquids to each section. First, second, and third fluid sealing connectors, such as diaphragms or membranes 70, 72, 74, are operatively associated with a top surface of the rectangular channel and are positioned at the approximate center of the first, second, and third washing sections 42, 44, 46, respectively. When the racks 50 are inserted into each washing section, each has an inlet aperture which registers with the membrane beneath that particular washing section. Under fluid pressure, the membranes expand and seal around the inlet aperture directing washing liquid into manifolds 75 which direct water to each spindle 58 of the racks. Spray from the nozzles 59 on each spindle assure that the interior of each piece of glassware is thoroughly washed.

Figure 3:
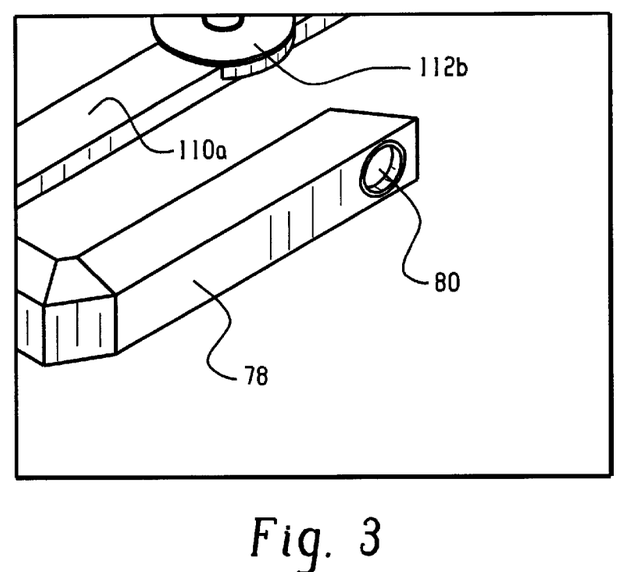
FIG. 3 is a partial perspective view of a channel having a valve in accordance with the present invention.
Figure 5:
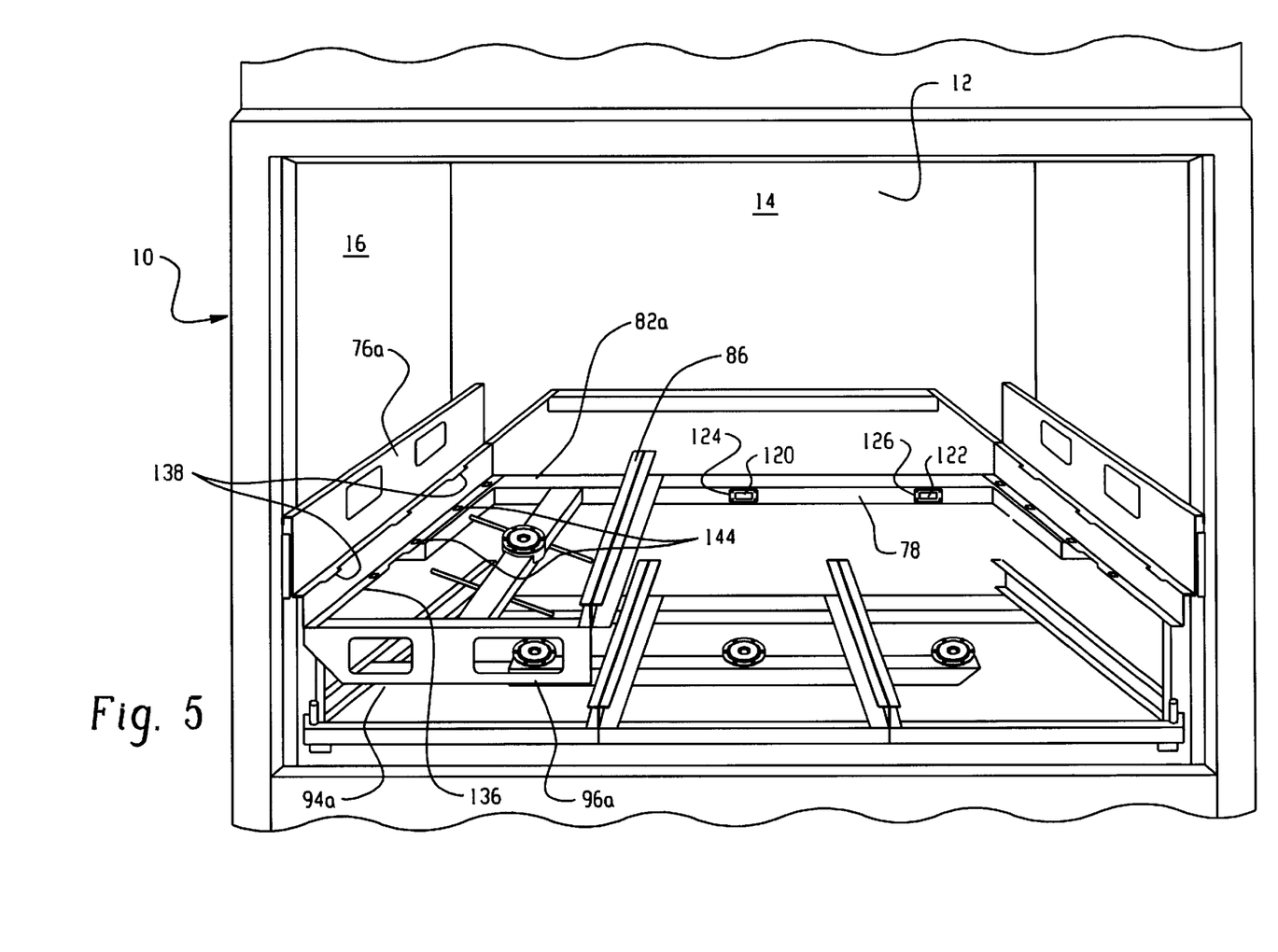
FIG. 5 is a perspective view of the washing device with the upper shelf pulled half way out and its second and third shelf sections removed.

The upper shelf 30 is disposed vertically above the lower shelf and has first and second side support members 76a, 76b which slidably connect the upper shelf to the opposing sidewalls 16, 18 at a predetermined or adjustable height. Since the upper shelf is slidably connected to the opposed sidewalls 16, 18, the entire upper shelf is capable of sliding in and out of the washing chamber as shown in FIG. 5. A channel 78 extends across the back edge of the upper shelf and bends forward 90° upon reaching members 76a, 76b. After bending 90°, the channel terminates below the side support members at a predetermined location. An inlet valve 80 (see FIG. 3) is located on a side surface of the channel which allows water, soap, etc. to enter the channel. The channel then distributes the washing liquids around the upper shelf.

The upper shelf 30 comprises a first shelf section 82a, a second shelf section 82b, and a third shelf section 82c. Although the upper device will be described having three shelf sections, it will be understood that any number of shelf sections, such as two or four, is contemplated by the present invention. First and second oppositely faced tracks or C-channels 86, 88, identical to the tracks 40 used for the lower shelf 32, are mounted back to back and effectively partition the first and second shelf sections 82a, 82b. Similarly, third and fourth oppositely faced tracks 90, 92 effectively partition the second and third shelf sections 82b, 82c. Spindle headers or racks 50, identical to those used for the lower shelf 32, are carried by each shelf section.

Each shelf section includes a front member 94a, 94b, 94c having an effective width equal to the width of a rack 50. The front member comprises a vertical face 96a, 96b, 96c and upper and lower backwardly extending flanges. Each front member defines two substantially rectangular openings. On the first and the third shelf sections 82a, 82c, the face of the front member has a canted outer edge 98a, 98c.

Each shelf section further includes a hollow rectangular beam 110a, 110b, 110c extending longitudinally between their front member 94a, 94b, 94c and channel 78 in order to provide water, soap, etc. to the shelf sections. First, second, and third fluid sealing connectors 112a, 112b, 112c, such as membranes or diaphragms, each having a fluid outlet are operatively associated with an approximate center of the rectangular beams 110a, 110b, 110c respectively. As the fluid pressure in the sealing connectors increases, the connectors expand and seal around the inlet aperture of an associated rack, thereby directing washing liquid from the fluid outlets into the rack manifolds 75 which direct water to each spindle 58 of the racks.

Figure 4:
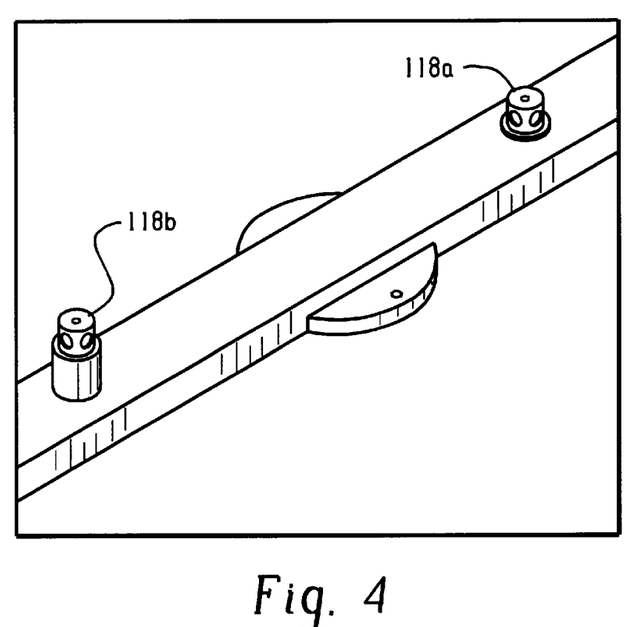
FIG. 4 is a lower perspective view of a portion of a hollow beam of a shelf section in accordance with the present invention.

First spray arms 114 and second spray arms 116 are rotatably mounted beneath each rectangular beam for providing water, soap, etc. to the exterior of the glassware articles. Holes are provided in the spray arms at a variety of locations for directing water, soap, etc. in all directions. The first and second spray arms are mounted on first and second hubs 118a, 118b (see FIG. 4) respectively, which rotate the first and second spray arms in different horizontal planes in order to prevent them from colliding.

Figure 6:
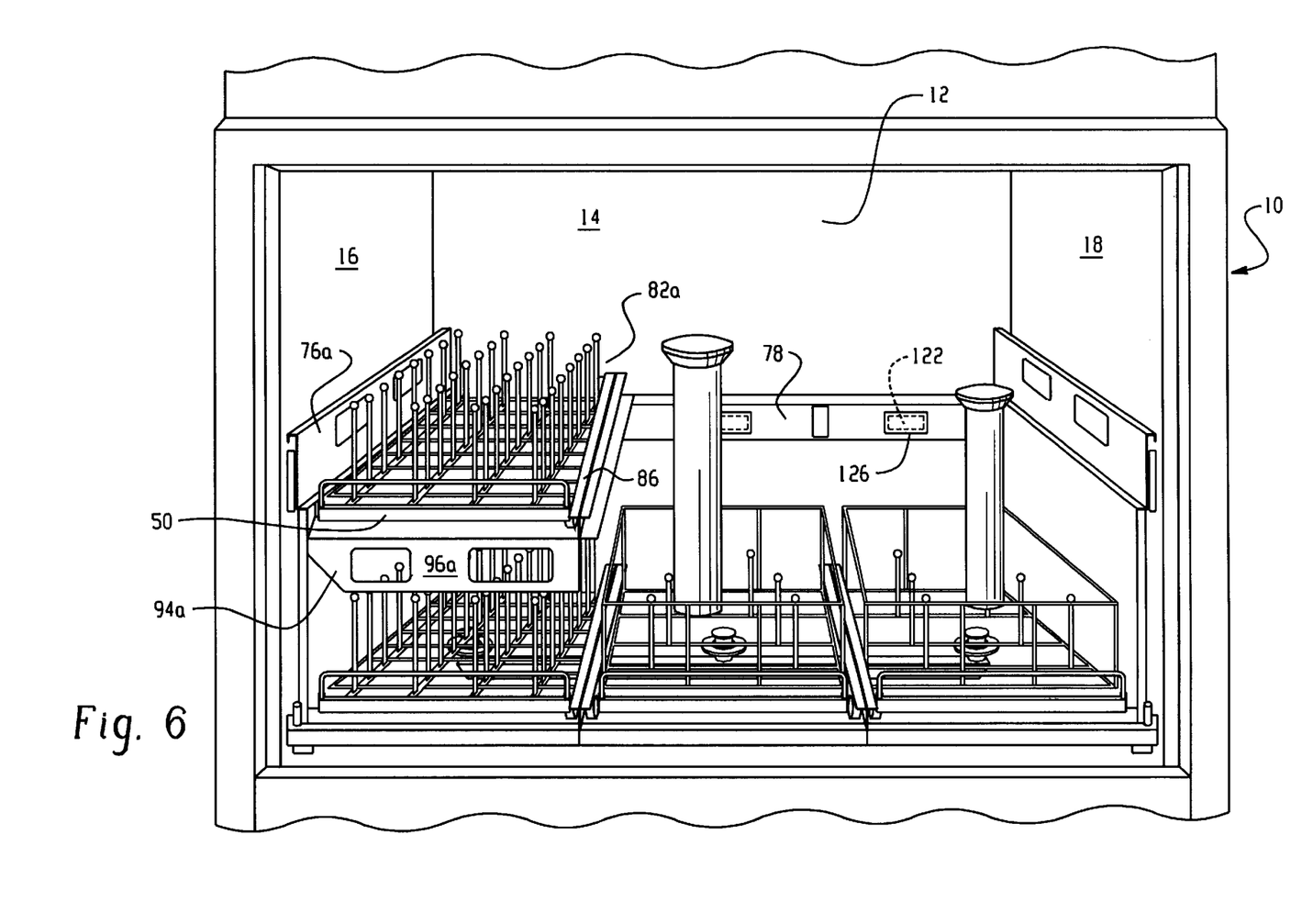
FIG. 6 is a front perspective view of the washing device with two sections of the upper shelf removed accommodating relatively large glassware articles.

In order to accommodate glassware articles having a height greater than the distance between the upper and lower shelves 30, 32 or the upper shelf and the top wall 20, the second and third shelf sections 82b, 82c are individually removable. With reference to FIGS. 5 and 6, the washing device is shown with the second and third shelf sections removed. With both the second and third shelf sections removed, the washing chamber 12 can accommodate small, medium, and large articles simultaneously.

To allow insertion and removal of the second and third shelf sections, first and second openings 120, 122 are provided in channel 78 for receiving the hollow rectangular beams 110b, 110c of the second and third shelf sections 82b, 82c respectively. First and second flap valves 124, 126 are mounted to channel 78 to close the first and second openings 120, 122 when a self section is removed. When it is desired to use the second and third shelf sections, they are inserted into the valves 124, 126, respectfully, and suspended in the washing chamber in a cantilevered manner.

Removing the second and third shelf sections merely requires an operator to manually urge the rectangular beams 110b, 110c from the first and second openings 120, 122 respectfully. Because the sections comprise only one third of the entire upper shelf, they are relatively easy to handle and remove when compared to an entire upper shelf. As illustrated, racks for larger articles having fewer spindles which are spaced further apart from one another can be used when the second and/or third shelf section(s) is/are removed.

With continued reference to FIGS. 5 and 6, the first shelf section 82a is preferably a rigid non-removable structure. However, the washing device can be designed having a removable first section if desired. The first support member 76a has a flat bottom surface 136 which forms the outer edge of the first shelf section 82a. The flat bottom surface of the first support member and a lower flanged portion of the first track 86 support a rack 50 carried by the first shelf section. A series of tabs 138 extend horizontally inward from the first support member which with bottom surface 136 prevents substantial vertical movement of the rack 50 at the outer edge of first shelf section. Upper and lower flanges of the first C-channel prevent vertical movement of the rack at the inner edge of the first shelf section. To prevent forward and backward movement of a rack during washing operations, the wheels 52 of the rack fall into apertures 144 located at predetermined positions along surface 136 and the lower flange of the first C-channel. Alternatively, recesses, protrusions, or bumps may be provided to hinder forward and backward movement of the racks.

Figure 8:
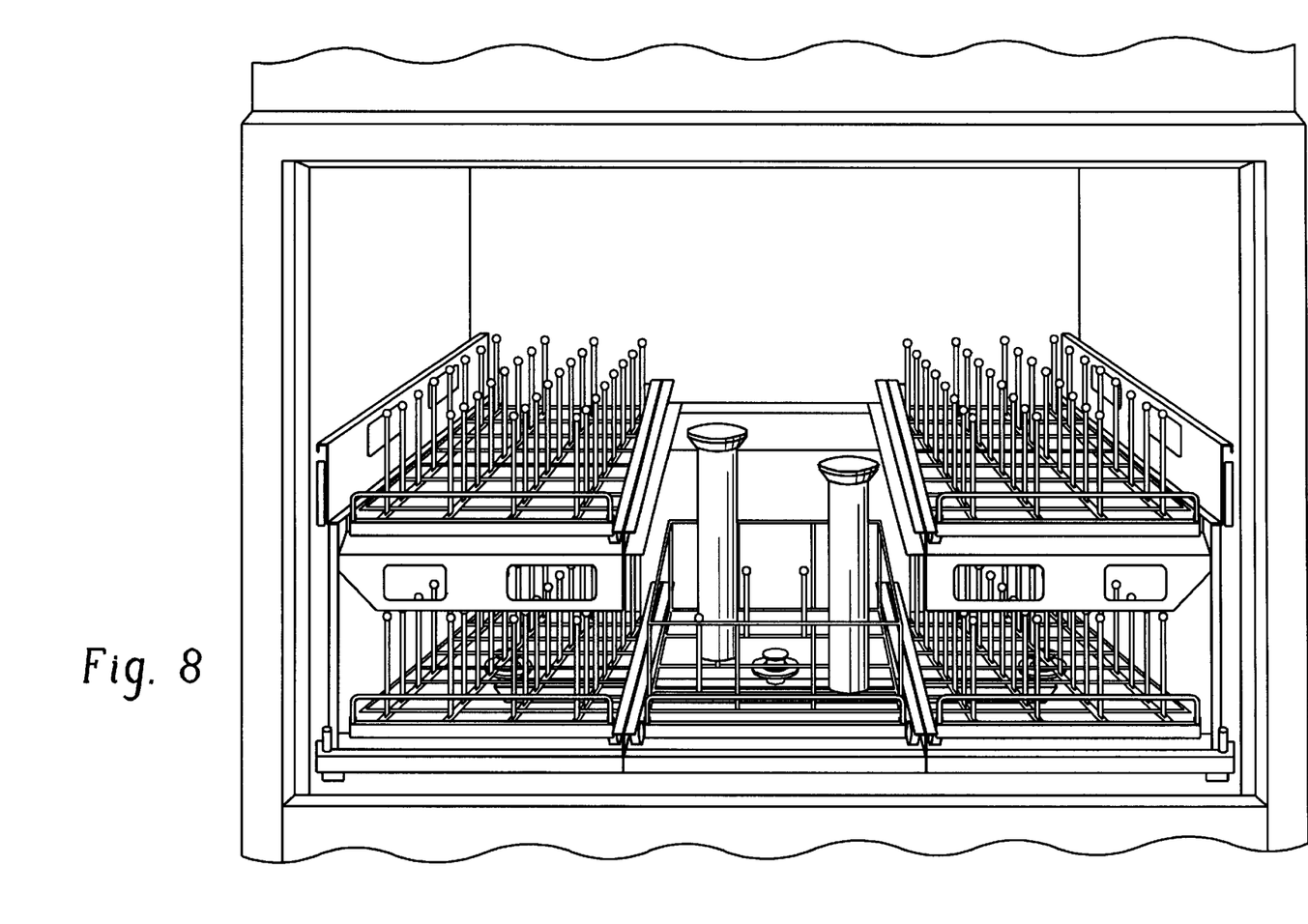
FIG. 8 is a front perspective view of the washing device showing the second (middle) upper shelf section removed and the other sections loaded with spindle headers.

If only a few large glassware articles need to be cleaned, it may be desirable to remove only one shelf section in order to maximize the device's washing potential. When two upper shelf sections are being used, the third section 82c is preferably placed in the washing chamber 12 along with the first section 82a (see FIGS. 8 and 9). However, any two sections may be used without going outside the scope and meaning of the present invention.

Figure 7:
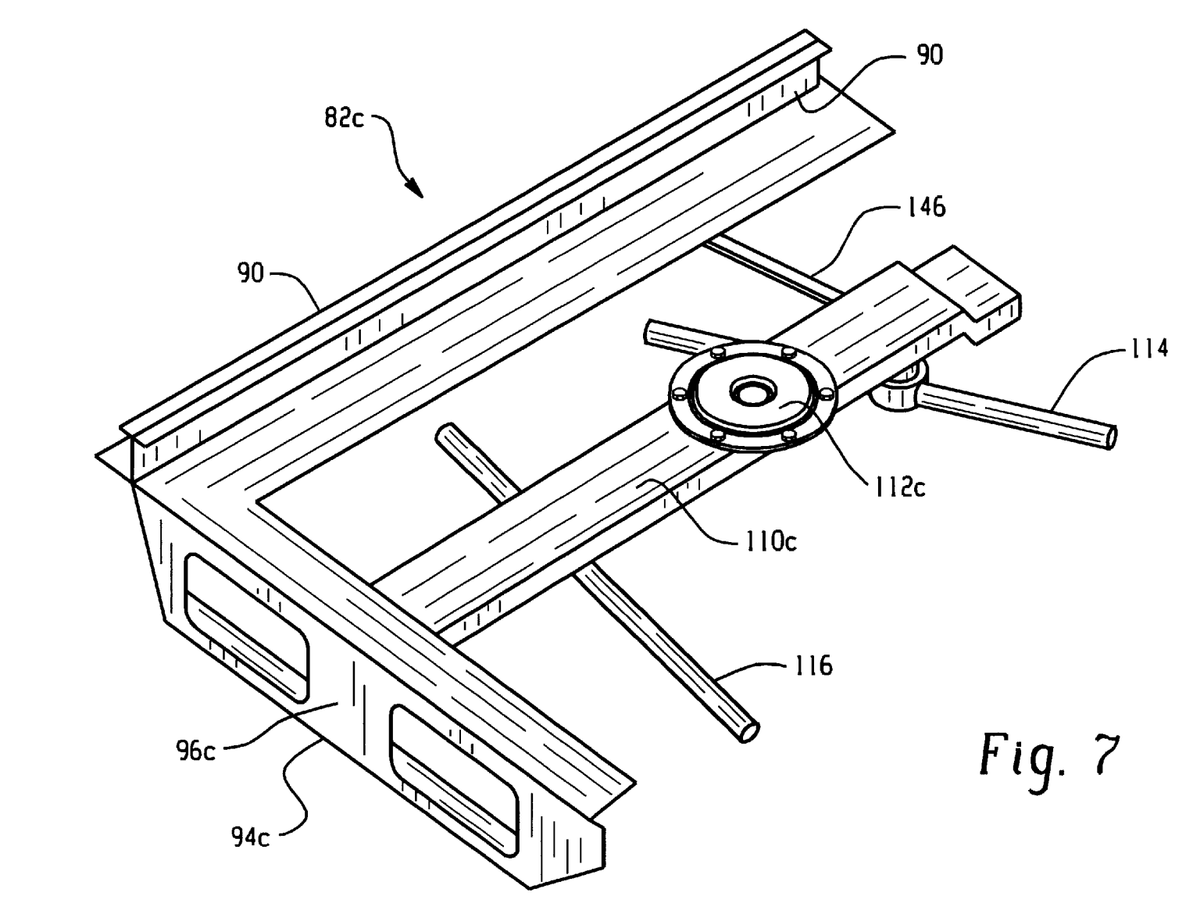
FIG. 7 is a perspective view of a third (right) upper shelf section viewed from below.

Turning now to FIG. 7, the third shelf section 82c comprises the opposed third and fourth tracks 90, 92 which extend backwardly from a top surface of front member 94c. In addition hollow rectangular beam 110c extends backwardly from a central portion of front member 94c. Just before terminating, the rectangular beam bends downward, preferably 45°, and then back to horizontal; Such a design facilitates insertion of the rectangular beam into the opening of the second valve 126. The third diaphragm 112c is operatively associated with a top surface of rectangular beam 110c. First and second spray arms 114, 116 are rotatably mounted beneath rectangular beam 110c on horizontal planes different from one another. A guiding bar 146 extends between the rectangular beam and the opposed tracks to maintain the appropriate spacing therebetween and to facilitate proper alignment when the third shelf member is placed into the washing chamber.

Figure 9:
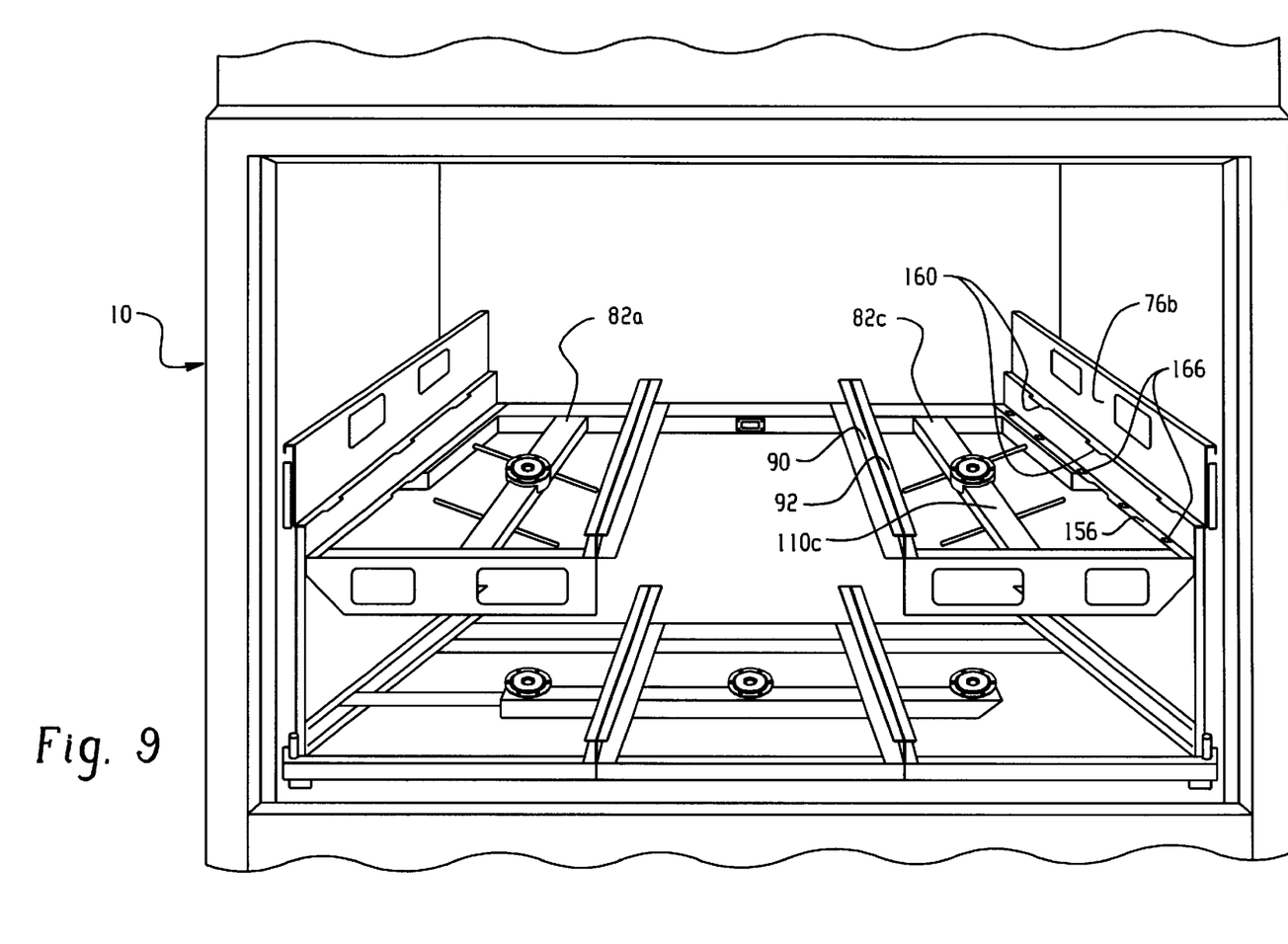
FIG. 9 is a front perspective view of the washing device with the second (middle) upper shelf section removed and with spindle headers.
Figure 10:
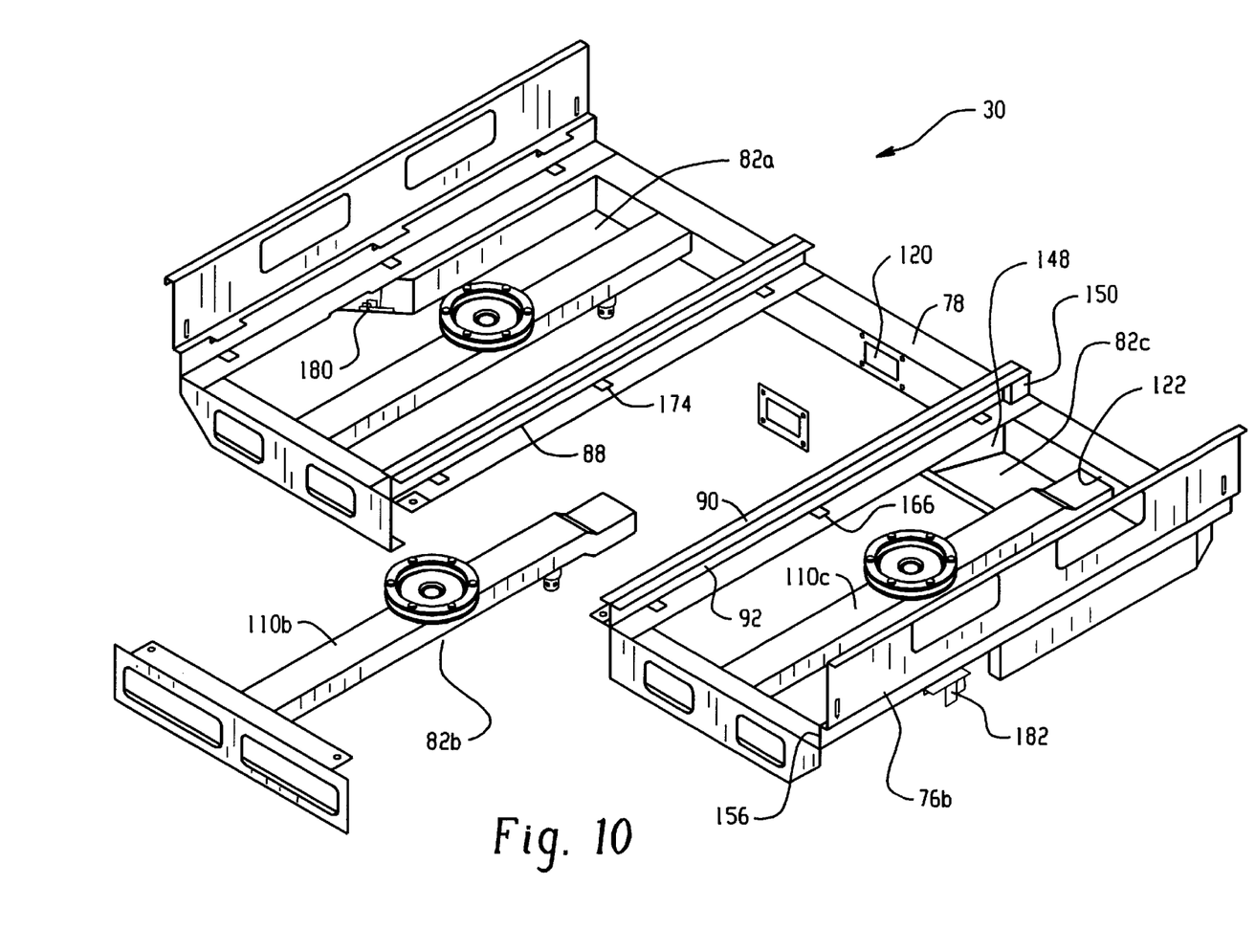
FIG. 10 is an expanded perspective view of the upper shelf with the center section pulled out.

With reference to FIGS. 9 and 10, when use of the third shelf section is desired, rectangular beam 110c of the third shelf section is inserted into the opening of the second valve 126 so that it is suspended in a cantilevered manner. Preferably, pinch fingers 150 are mounted to channel 78 to engage the ends of the opposed tracks and hold them in proper position.

Figure 11:
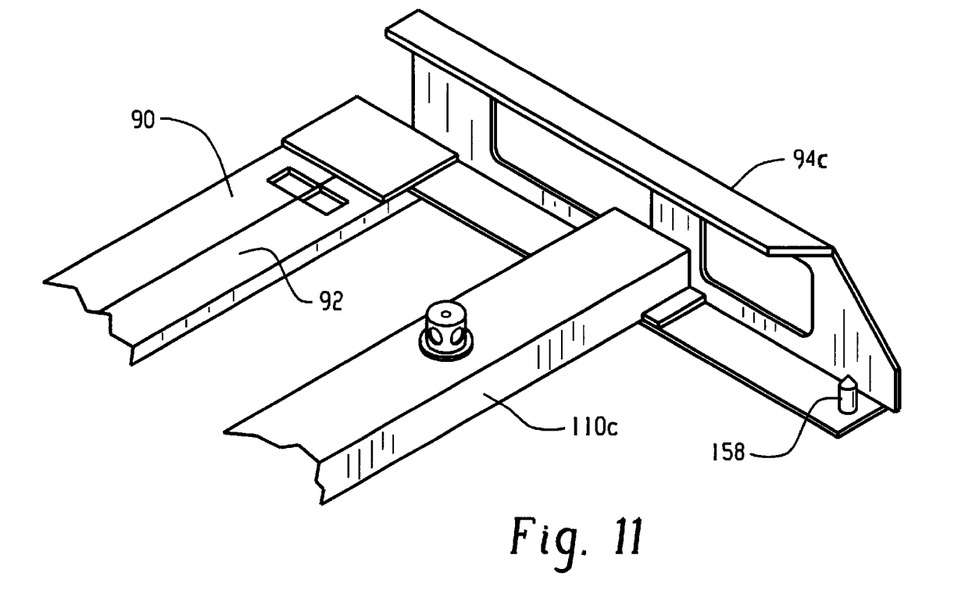
FIG. 11 is a perspective partial view of the third shelf section from below with the rotary sprayer removed.

The second support member 76b has a flat bottom surface 156 which forms the outer edge of the third shelf section 82c. A fastener 158 (see FIG. 11), extending from beneath the horizontal flange of front face 94c, connects the bottom surface 156 of the second support member to the first shelf section. The flat bottom surface 156 of the second support member and a lower flanged portion of the fourth track 92 are adapted to support a rack 50. A series of tabs 160 extend horizontally inward from the second support member which with bottom surface 156 prevents substantial vertical movement of the rack 50 at the outer edge of third shelf section. Upper and lower flanges of the fourth C-channel 92 prevents vertical movement of the rack at the inner edge of the first shelf section. To prevent forward and backward movement of the rack during washing operations, the wheels 52 of the rack fall into apertures 166 located at predetermined positions along surface 156 and the lower flange of the fourth C-channel. Alternatively, recesses, protrusions, or bumps may be provided to hinder forward and backward movement of the racks.

Figure 12:
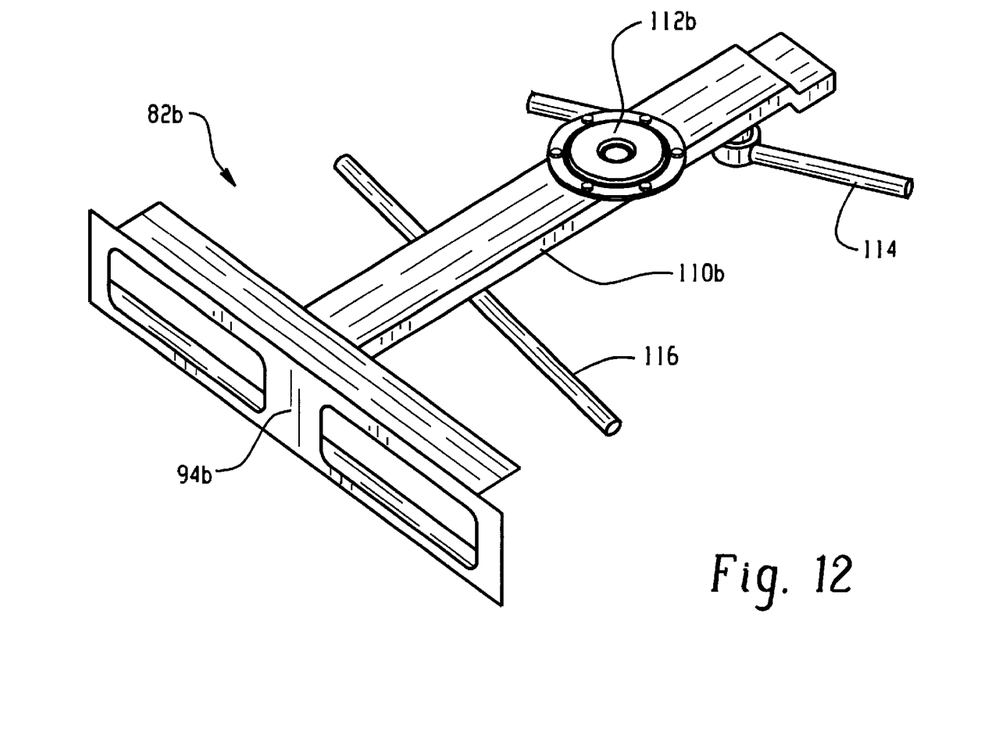
FIG. 12 is a perspective view of the second (middle) upper shelf section in accordance with the present invention.

If only relatively small glassware articles need be cleaned, the second shelf section 82b may be placed in the washing chamber with the first and third shelf sections 82a, 82c (see FIGS. 1 and 2). Referring to FIG. 12, the second shelf section comprises rectangular hollow beam 110b extending from front member 94b. Just before terminating, the rectangular beam bends downward, preferably 45°, and then back to horizontal. The second diaphragm 112b is operatively associated with a top surface of rectangular beam 110b. The first and second spray arms 114, 116 are rotatably mounted beneath rectangular beam 110b on horizontal planes different from one another.

Figure 13:
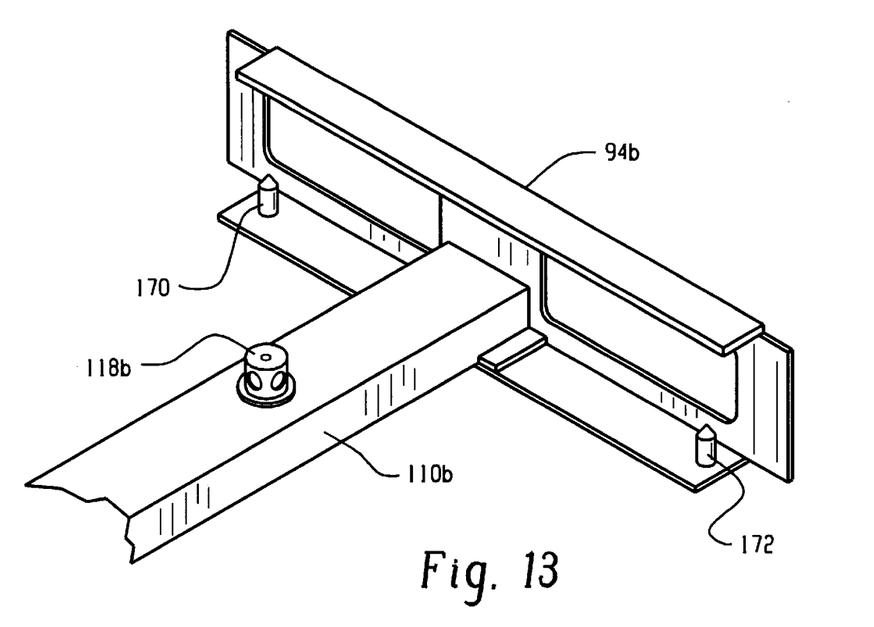
FIG. 13 is a perspective partial view of the second shelf section viewed from below.

Turning back to FIG. 10, rectangular beam 110b is inserted into the opening of the valve 124 when use of the second shelf section is desired. The second and third tracks 88 and 90 form the outer edges of the second shelf section once the second shelf section has been fully inserted. Fasteners 170, 172 (see FIG. 13), extending from beneath the flange of front member 94b, attach the second shelf section to the second and third tracks 88, 90. In order to prevent forward and backward movement of the rack 50, the wheels 52 of the rack fall into apertures 174 provided in the lower flanges of the second and third tracks. Additionally, the upper and lower flanges of tracks 88, 90 prevent substantial vertical movement of the rack during washing operations.

Figure 14:
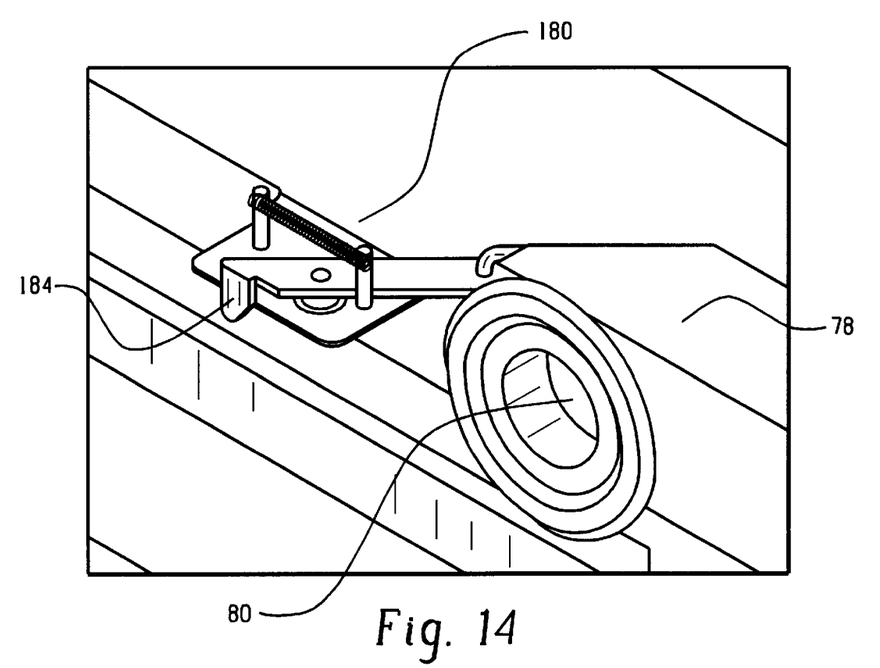
FIG. 14 is an enlarged view of a locking assembly for locking/releasing the upper shelf as a whole from the washer.

When it is desirable to use only the lower shelf 32, the upper shelf may be completely removed. First and second locking assemblies 180, 182 are mounted to the two support members 76a, 76b respectively for allowing removal of the upper shelf. Preferably, each locking assembly includes a lever 184 (see FIG. 14) which is manually activated to unlock the top shelf and allow it to be removed. However, any known locking assembly is within the scope of the present invention.

The present invention provides a washing device capable of sanitizing small, medium, and large glassware articles simultaneously in a multi-level system, thereby maximizing the efficiency and washing potential of the machine. In addition, because the shelf assembly is divided into relatively small and easy to handle sections, the required number of workers to operate the machine is minimized. Importantly, the invention can be incorporated into already existing machines.

The present invention has been described with reference to the preferred embodiment. Obviously, modifications and alterations will occur to others upon reading and understanding the preceding detailed description. For example, the upper shelf could be manufactured with more or less than three shelf sections. In addition, the washing device could be manufactured with more or less than two shelves. It is intended that the invention be construed as including all such modifications and alterations insofar as they come within the scope of the appended claims or the equivalents thereof.

Having thus described the preferred embodiments, the invention is now claimed to be:

1. A washer comprising:
    a washing chamber defined by a series of walls,
    a first shelf mounted within the washing chamber having at least one shelf section for receiving and supporting articles to be cleaned during a washing operation, and
    a second shelf mounted within the washing chamber vertically above the first shelf, the second shelf having at least two shelf sections, at least one of the at least two shelf sections being selectively detachable from the second shelf and removable from the washing chamber so that additional space may be provided for larger articles on one side of the first shelf.

2. The washer according to claim 1, further comprising a series of removable racks that are received by the at least one shelf section of the first shelf and the shelf sections of the second shelf, the racks having a plurality of vertically extending spindles over which glassware is placed, the racks differing in spindle size and spindle spacing for accommodating different sizes of glassware.

3. The washer according to claim 2, wherein the at least one washing section of the first shelf and the shelf sections of the second shelf each include a front member and a hollow washing fluid carrying beam extending therefrom.

4. A washer comprising:
    a washing chamber;
    a lower shelf mounted within the washing chamber having at least one lower shelf section for receiving and supporting articles to be cleaned during operation of the washer, and
    first and second upper shelf sections mounted in the washing chamber above the lower shelf, the second upper shelf section being selectively detachable and removable from the washing chamber so that additional space may be provided for larger articles on one side of the lower shelf, the first upper shelf section including:
        a washing liquid outlet defined in a hollow beam for providing a decontamination solution to articles to be cleaned; and
    a rack received by the second shelf section, the rack including:
        a plurality of spindles, and
        a manifold with a washing liquid inlet that communicates with the washing liquid outlet, the manifold conveying received washing liquids to nozzles in the spindles.

5. The washer according to claim 3, wherein at least one spray arm is rotatably mounted to the hollow beam of each shelf section of the second shelf.

6. The washer according to claim 3, further comprising a channel disposed around at least a portion of the periphery of the second shelf for providing decontamination solutions to the second shelf.

7. The washer according to claim 6, wherein the channel has a series of openings that communicate with an open end of the hollow beams of the shelf sections of the second shelf so that washing solutions can be provided from the channel to each of the shelf sections.

8. The washer according to claim 7, wherein the shelf sections of the second shelf are removable by manually urging the hollow beam of the shelf section to be removed from the corresponding opening of the channel and wherein the channel includes valves which close when the shelf sections are removed.

9. The washer according to claim 2, wherein each of the shelf sections of the second shelf has horizontally spaced first and second surfaces for supporting the racks.

10. The washer according to claim 9, wherein the horizontally spaced first and second surfaces include a series of impediments which prevent forward and backward movement of the racks during operation.

11. The washer according to claim 1, wherein the entire second shelf is removable from the washing chamber.

12. The washer unit according to claim 11, wherein a pump selectively operable between a first low speed and a second high speed comnmunicates with the first and second shelves and pumps cleaning solutions through the washing chamber, the pump operating in low speed when the second shelf is removed from the washing chamber and high speed when the second shelf is in use.

13. A shelving assembly for a liquid cleaning unit comprising:
    a shelf having at least two shelf sections, each of the at least two shelf sections having a surface for carrying a set of articles to be cleaned, at least one of the at least two shelf sections being detachable and removable from the shelf;
    a channel fluidly connected to each of the at least two shelf sections for providing cleaning solutions to the articles to be cleaned; and
    at least one support member mounted to an outer edge of the shelf for allowing the shelf to be slidably mounted within a cleaning unit.

14. The shelving assembly according to claim 13, wherein the shelf sections of the shelf each include a front member and a hollow beam extending therefrom.

15. The shelving assembly according to claim 14, wherein a cleaning liquid outlet is provided in each hollow beam of the shelf sections of the shelf.

16. The shelving assembly according to claim 14, wherein at least one spray arm is rotatably mounted to the hollow beam of each shelf section.

17. The shelving assembly according to claim 14, further comprising a channel disposed around at least a portion of the periphery of the shelf for providing decontamination solutions to the hollow beams of the shelf.

18. The shelving assembly according to claim 17, wherein the shelf sections of the shelf are removable by manually urging the hollow beam of the shelf section to be removed from a corresponding opening in the channel.

19. A shelving assembly for a liquid cleaning unit comprising:
    a shelf having at least two shelf sections for supporting articles, at least one of the at least two shelf sections being detachable and removable from the shelf;
    a channel associated with each of the at least two shelf sections for providing cleaning solution to the articles to be cleaned; and
    at least one support member mounted to an outer edge of the shelf for allowing the shelf to be slidably mounted within a cleaning unit; and
    removable racks that are received by the shelf sections of the shelf, the racks having a plurality of vertically extending spindles over which articles are placed, the racks differing in spindle size and spindle spacing for accommodating different sizes of article.

20. The shelving assembly according to claim 19 wherein:
    a washer liquid outlet is defined in each hollow beam of the shelf sections of the second shelf for providing decontamination solution to articles to be cleaned;
    each rack received by the second shelf section includes a manifold with a washing liquid inlet that communicates with the washing liquid outlet, the manifold conveying received washing liquids to nozzles in the spindles.

* * * * *